US012685643B2

(12) United States Patent
Rister

(10) Patent No.: US 12,685,643 B2
(45) Date of Patent: Jul. 21, 2026

(54) DUAL MOBILITY ACETABULAR IMPLANT FOR HIP REVISION SURGERY

(71) Applicants:Smith & Nephew, Inc., Memphis, TN (US); Smith & Nephew Orthopaedics AG, Zug (CH); Smith & Nephew Asia Pacific Pte. Limited, Singapore (SG)

(72) Inventor: David W. Rister, Nesbit, MS (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 504 days.

(21) Appl. No.: 18/272,953

(22) PCT Filed: Jan. 14, 2022

(86) PCT No.: PCT/US2022/012448
§ 371 (c)(1),
(2) Date: Jul. 18, 2023

(87) PCT Pub. No.: WO2022/159340
PCT Pub. Date: Jul. 28, 2022

(65) Prior Publication Data
US 2024/0074864 A1 Mar. 7, 2024

Related U.S. Application Data

(60) Provisional application No. 63/138,893, filed on Jan. 19, 2021.

(51) Int. Cl.
A61F 2/32 (2006.01)
A61F 2/30 (2006.01)
A61F 2/34 (2006.01)

(52) U.S. Cl.
CPC .. *A61F 2/30734* (2013.01); *A61F 2002/3069* (2013.01); *A61F 2002/3079* (2013.01); *A61F 2002/3208* (2013.01); *A61F 2002/3448* (2013.01); *A61F 2002/345* (2013.01)

(58) Field of Classification Search
CPC ...... A61F 2002/3208; A61F 2002/3448; A61F 2002/345; A61F 2/34; A61F 2/30734;
(Continued)

(56) References Cited

U.S. PATENT DOCUMENTS 8,465,549 B2 * 6/2013 Richardson ............... A61F 2/32
623/22.17
9,445,905 B2 9/2016 Muratoglu
(Continued)

FOREIGN PATENT DOCUMENTS

CN 204411029 6/2015
EP 3721837 A1 10/2020
(Continued)

OTHER PUBLICATIONS

International Search Report and Written Opinion for Application No. PCT/US2022/012448 dated Apr. 4, 2022.
(Continued)

*Primary Examiner* — Bruce E Snow
(74) *Attorney, Agent, or Firm* — KDW Firm PLLC

(57) ABSTRACT
An insert (240) arranged and configured for use in a dual mobility acetabular implant (100) is disclosed. The insert includes a plurality of chamfers (260, 262, 264) arranged and configured to contact the femoral neck (172) and/or head (170) of a femoral implant (175). The insert includes a plurality of chamfers such as, for example, two or three chamfers to define a plurality of differently arranged contact surfaces for contacting the femoral component to accommodate a variety of different femoral component configu-
(Continued)

rations and/or impingement conditions in order to reduce contact stress between the insert and the femoral component.

8 Claims, 11 Drawing Sheets

(58) Field of Classification Search
CPC ...... A61F 2002/3069; A61F 2002/3079; A61F 2/30767; A61F 2/32; A61F 2/3609; A61F 2002/3093; A61F 2002/30985
See application file for complete search history.

(56) References Cited

U.S. PATENT DOCUMENTS

| | | |
|---|---|---|
| 2014/0128988 A1 | 5/2014 | Muratoglu |
| 2019/0254827 A1* | 8/2019 | Rister ........................ A61F 2/34 |
| 2024/0074864 A1* | 3/2024 | Rister ................ A61F 2/30734 |

FOREIGN PATENT DOCUMENTS

| | | |
|---|---|---|
| JP | 2011087712 A | 5/2011 |
| WO | 2018075478 A1 | 4/2018 |

OTHER PUBLICATIONS

Nebergall, Audrey et al., "Analysis of Dual Mobility Liner Rim Damage Using Retrieved Components and Cadaver Models," The Journal of Arthoplasty, Dec. 22, 2015.

Di Laura, Anna et al., "Retrieval evidence of impingement at the third articulation in contemporary dual mobility cups for total hip arthoplasty," International Orthopedics, Jun. 4, 2017.

Scott, Trevor et al., "A Retrieval Analysis of Impingement in Dual-Mobility Liners," The Journal of Arthoplasty, Mar. 6, 2018.

* cited by examiner

DUAL MOBILITY ACETABULAR IMPLANT FOR HIP REVISION SURGERY

CROSS-REFERENCE TO RELATED APPLICATIONS

This application is a National Phase filing of International Application No. PCT/US2022/012448, filed Jan. 14, 2022, which is a non-provisional of, and claims the benefit of the filing date of, U.S. provisional patent application No. 63/138,893, filed Jan. 19, 2021, entitled "Dual Mobility Acetabular Apparatus for Hip Revision Surgery," the entirety of each application is incorporated by reference herein.

FIELD OF THE DISCLOSURE

The present disclosure relates generally to orthopedic apparatuses and methods to address acetabular defects, and particularly to a dual mobility acetabular implant incorporating a dual mobility bearing incorporating an insert having a variable geometry arranged and configured to interact with a variety of femoral components.

BACKGROUND OF THE DISCLOSURE

Articulating regions of a patient's anatomy can include areas where two bone sections move relative to each other. For example, an acetabulum can provide a region for articulation with a femoral head. The articulating region, however, can become injured or worn, and thus require replacement with one or more implants. Such implants can replace the acetabulum, the femoral head, and various other portions of the femur, or other combinations thereof. The replacement of both the acetabulum and the femoral head is generally referred to as a total joint replacement.

Acetabular implants, apparatuses, prostheses, or devices (used interchangeably herein without the intent to limit) are one type of implant currently used to address acetabular defects in which large portions of a patient's medial wall are missing. Recently, referring to FIG. 1, dual mobility acetabular implants 100 have been developed. Dual mobility acetabular implants 100 have shown promise in reducing the rate of dislocation by introducing increased femoral head sizes as compared to conventional acetabular apparatuses. Generally speaking, as shown, current dual mobility acetabular implants 100 include an acetabular cup or shell 110 for implanting into a patient's acetabular region, a liner 120 arranged and configured to be inserted inside of the cup 110, and a dual mobility bearing including an insert 140 arranged and configured to be inserted inside of the liner 120 and a femoral head 170 of, for example, a hip implant 175.

In use, the acetabular cup or shell 110 (used interchangeably herein without the intent to limit) is implanted into the patient's acetabular region. The acetabular cup 110 may be secured to the patient's acetabulum via, for example, fasteners, adhesive, cement, etc. Next, a liner 120 is implanted into the acetabular cup 110. In use, the liner 120 may be coupled to the cup 110 via, for example, an adhesive, cement, etc. Thus, the liner 120 may be inhibited from moving, articulating, or the like, relative to the cup 110.

Subsequently, the dual mobility bearing is positioned within the liner 120. In addition, the dual mobility bearing is arranged and configured to receive the femoral neck 172 of, for example, the hip implant 175. In use, the dual mobility bearing includes an insert 140 and a femoral head 170, the insert 140 is arranged and configured to articulate relative to the liner 120. Moreover, the femoral head 170 is arranged and configured to articulate relative to the insert 140. Thus arranged, dual mobility acetabular implants 100 utilize two points of articulation to provide increased range of motion. That is, dual mobility acetabular implants 100 enable articulation between the femoral head 170 and the insert 140, and between the insert 140 and the liner 120 (e.g., insert 140 includes a convex, generally spherical outer bearing surface, which articulates against the concave, generally hemispheric, interior cavity of the liner 120 and a concave, generally spherical, inner bearing surface which articulates against the convex, outer surface of the femoral head 170, which is coupled to the femoral neck 172 of the hip implant 175).

Generally speaking, the majority of articulation in the hip is shared between the inner and outer bearing surfaces of the insert 140. The majority of articulation occurs at the inner bearing surface (e.g., articulating bearing surface between the interior cavity of the insert 140 and the outer bearing surface of the femoral head 170), a lesser degree of articulation occurs at the larger, outer bearing surface of the insert 140 (e.g., articulating bearing surface between the interior cavity of the liner 120 and the outer bearing surface of the insert 140). Motion along the outer bearing surface may be generated by a plurality of biomechanical forces or design features inclusive of, but not limited to, a moment created by an offset between the centers of rotation of the inner and outer bearing surfaces, direct impingement with the femoral neck, excess friction at the inner femoral head (e.g., inner bearing surface), or a combination of such forces within the joint. When impingement contact occurs between the neck of the femoral component, it occurs at the annular orifice, rim, entrance, mouth, etc. (terms used interchangeably herein without the intent to distinction) of the insert 140. If excessive or repeated contact occurs, damage to the insert 140 may occur thereby reducing the inserts 140 ability to constrain the femoral head 170, which may increase the risk of intraprosthetic dissociation or dislocation of the femoral head 170 from the insert 140 ("IPD").

Many orthopaedic manufacturers provide a variety of femoral implants to address a variety of different disease states. Within each of these implant families, a variety of femoral neck geometries exist with changing lengths, neck angles, tapers, and varied cross-sectional geometries along the femoral neck from the stem of the femoral component to the coupling mechanism (e.g., taper locking mechanism, etc.), which mechanically couples the femoral head. In addition, femoral heads may be offered with a variety of distances between the coupling mechanism and the center of rotation of the femoral head, which effectively changes the length of the femoral neck. The modularity of the femoral components (e.g., stem and femoral heads) provide great flexibility during surgery to reconstitute the natural anatomy of the patient's hip. However, this variety of options presents a myriad of different impingement conditions, each one presenting unique wear and/or damage conditions.

Generally speaking, to address this concern, due to the variety of impingement conditions provided by orthopaedic hip arthroplasty implant systems, current inserts 140 include a singular annular chamfer at the rim of the insert 140. This single chamfer may, however, result in relatively high contact stress conditions for a number of implant combinations. That is, orthopaedic manufacturers have incorporated a single chamfer into the insert 140. However, the chamfer is generally designed based upon one particular or anticipated condition (e.g., chamfer has been designed with a particular femoral neck and femoral head combination). In use, as surgeons utilize different sized components, the insert's chamfer may not be properly designed for the actual femoral neck and femoral head combination being utilized thus resulting in increased contact stresses between the insert 140 and the femoral neck 172. For example, it has been found that increased deformation may occur along the insert's chamfer due to the reduced contact area between the femoral neck 172 and the insert 140. That is, it has been found that incorporation of a single chamfer may cause focal impingement at the femoral neck 172 leading to damage such as, for example, a raised rim and localized failure.

Thus, it would be beneficial to provide an insert for use in a dual mobility acetabular implant that is arranged and configured to reduce contact stress between the insert and the femoral neck for a variety of impingement conditions.

SUMMARY OF THE DISCLOSURE

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

The present disclosure provides a dual mobility acetabular implant arranged and configured to be implanted into a patient's bone (e.g., a patient's acetabulum). The dual mobility acetabular implant including an improved insert including a plurality of chamfers such as, for example, two or three chamfers to define a plurality of differently arranged contact surfaces or areas such as, for example, two, three, four, or more contact surfaces arranged and configured to contact the femoral neck. Thus arranged, by incorporating a plurality of chamfers defining a plurality of contact surfaces, the insert is arranged and configured to better accommodate a variety of different component configurations and/or impingement conditions provided by orthopaedic hip arthroplasty implant systems thereby reducing contact stress between the insert and the femoral neck during use.

That is, in one embodiment, an insert arranged and configured for use in a dual mobility acetabular bearing for incorporation into a dual mobility acetabular implant is disclosed. The insert includes a plurality or multiple chamfers positioned at the rim of the insert. Thus arranged, the insert provides multiple different and distinct contact surfaces for contacting the femoral neck or head of an associated hip implant system at the point of impingement with the insert. By providing increased contact surfaces, the insert is better able to accommodate any number of different femoral neck and head configurations as opposed to current inserts, which only utilize a single chamfer optimized for a limited number of femoral neck and head combinations.

In one embodiment, a dual mobility acetabular implant is disclosed. The dual mobility acetabular implant including an acetabular cup, a liner, and an insert. The acetabular cup being arranged and configured to be positioned within a patient's acetabulum, the acetabular cup including a body having an interior cavity. The liner being arranged and configured to be inserted into the interior cavity of the acetabular cup, the liner including a body having an interior cavity. The insert being arranged and configured to be inserted into the interior cavity of the liner, the insert including a body extending from an annular rim to a polar end, the body including an interior cavity, a convex exterior surface arranged and configured to articulate relative to an inner surface of the interior cavity of the liner, and a concave interior surface arranged and configured to receive and articulate relative to an outer surface of a femoral head. The annular rim of the insert including a plurality of chamfers defining multiple contact surfaces for contacting the femoral head or a portion of a femoral neck.

In one embodiment, the plurality of chamfers define a variety of geometries based on a variety of impingement conditions presented by families of femoral implants and femoral head designs.

In one embodiment, the multiple contact surfaces are arranged and configured to accommodate a variety of different femoral component configurations or impingement conditions in order to reduce contact stress between the insert and the femoral head or femoral neck.

In one embodiment, the plurality of chamfers include first, second, and third chamfers defining first, second, and third distinct contact surfaces, each of the first, second, and third distinct contact surfaces arranged and configured to contact the femoral head or femoral neck.

In one embodiment, each of the first, second, and third distinct contact surfaces is arranged and configured to contact the femoral head or femoral neck depending on a particular configuration of the femoral neck and femoral head used.

In one embodiment, the annular rim includes a first angled transition between the first and second contact surfaces and a second angled transition between the second and third contact surfaces.

In one embodiment, the annular rim includes a first radiused transition between the first and second contact surfaces and a second radiused transition between the second and third contact surfaces.

In one embodiment, the plurality of chamfers include first and second chamfers defining first and second distinct contact surfaces, each of the first and second distinct contact surfaces is arranged and configured to contact the femoral head or femoral neck.

In one embodiment, the first contact surface is arranged and configured to contact the femoral head or femoral neck during a first impingement condition and the second contact surface is arranged and configured to contact the femoral head or femoral neck during a second impingement condition.

In one embodiment, the dual mobility acetabular implant further includes a third chamfer defining a third contact surface, the third contact surface is arranged and configured to contact the femoral head or femoral neck.

In one embodiment, the third contact surface is arranged and configured to contact the femoral head or femoral neck during a third impingement condition.

In one embodiment, the insert includes an inner articulating surface arranged and configured to contact the femoral head and an outer articulating surface arranged and configured to contact the liner, wherein a rotational center point of the inner articulating surface is offset relative to a rotational center point of the outer articulating surface.

In one embodiment, the insert wherein a rotational center point of the inner bearing surface is offset relative to a rotational center point of the outer bearing surface.

In one embodiment, the insert is manufactured from a highly cross-linked ultra-high molecular weight polyethylene (UHMWPE). In addition, and/or alternatively, the insert includes a hydrophilic, low-friction bearing surface.

Embodiments of the present disclosure provide numerous advantages. For example, by providing a dual mobility acetabular implant with an insert including a plurality of chamfers defining multiple contact surfaces arranged and configured to contact the femoral neck and/or head, the insert is specifically designed to accommodate different neck and head combinations thus decreasing contact stress caused by various impingement conditions caused when the insert contacts the femoral neck and/or head thereby decreasing damage to the insert and preventing, or at least inhibiting, unintended escape or dislocation of the femoral head from the dual mobility acetabular implant (e.g., insert). That is, by incorporating multiple chamfers into the insert, the insert is specifically designed to account for a variety of neck lengths and geometries thereby reducing the potential for damage caused by periodic impingement contact between the femoral neck and insert.

Further features and advantages of at least some of the embodiments of the present disclosure, as well as the structure and operation of various embodiments of the present disclosure, are described in detail below with reference to the accompanying drawings.

BRIEF DESCRIPTION OF THE DRAWINGS

By way of example, a specific embodiment of the disclosed device will now be described, with reference to the accompanying drawings, in which.

Figure 1:
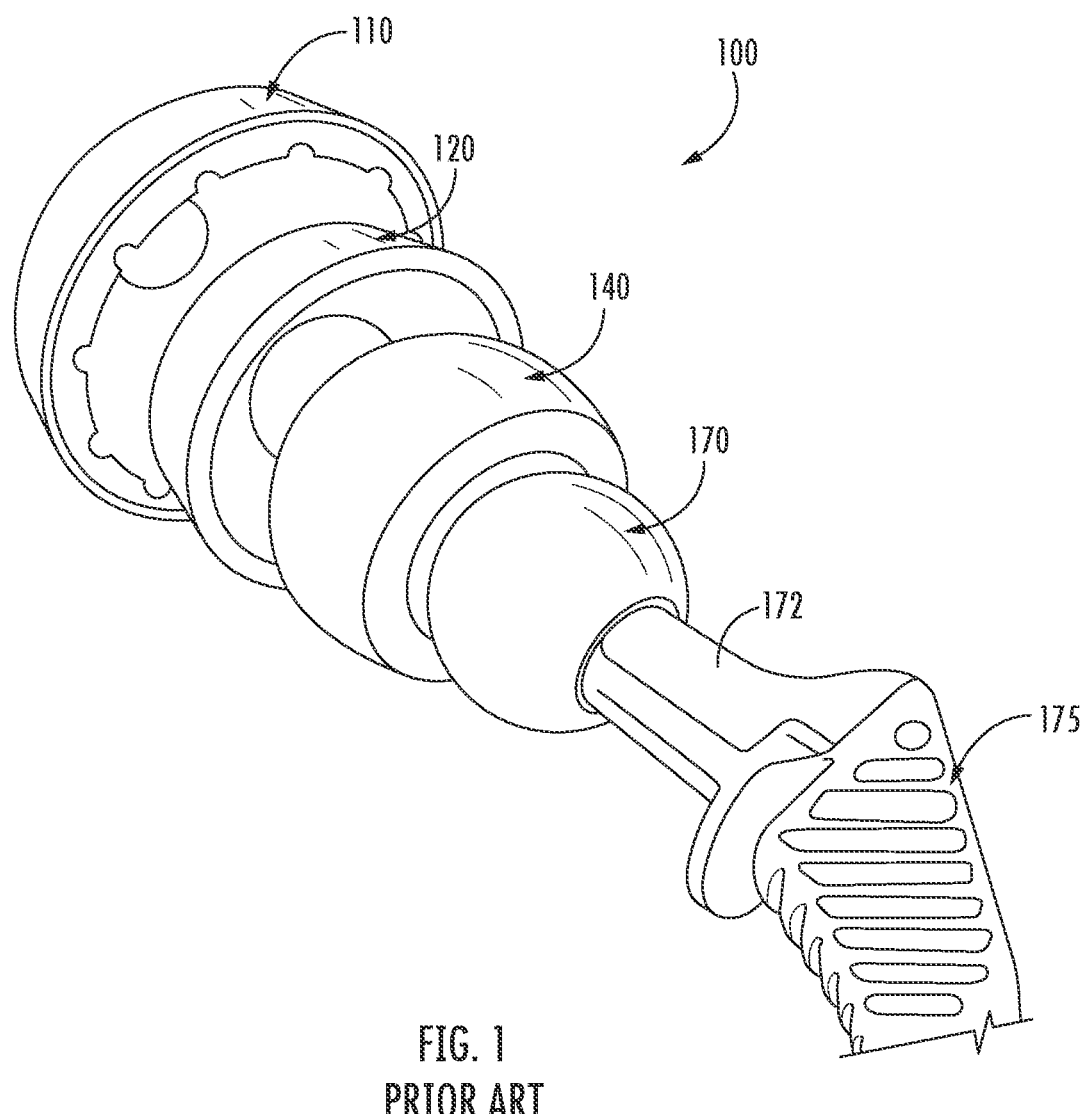
FIG. 1 shows an exploded, perspective view of a conventional dual mobility acetabular implant.

The drawings are not necessarily to scale. The drawings are merely representations, not intended to portray specific parameters of the disclosure. The drawings are intended to depict example embodiments of the disclosure, and therefore are not considered as limiting in scope. In the drawings, like numbering represents like elements.

Furthermore, certain elements in some of the figures may be omitted, or illustrated not-to-scale, for illustrative clarity. The cross-sectional views may be in the form of "slices", or "near-sighted" cross-sectional views, omitting certain background lines otherwise visible in a "true" cross-sectional view, for illustrative clarity. Furthermore, for clarity, some reference numbers may be omitted in certain drawings.

DETAILED DESCRIPTION

Embodiments of an improved dual mobility acetabular implant for hip revision surgery will now be described more fully hereinafter with reference to the accompanying drawings, in which preferred embodiments of the present disclosure are presented. More particularly, embodiments of an improved insert arranged and configured to be incorporated into a dual mobility acetabular implant will now be described more fully hereinafter with reference to the accompanying drawings, in which preferred embodiments of the present disclosure are presented. As will be described and illustrated, the improved insert includes a plurality of chamfers such as, for example, two or three chamfers to define a plurality of differently arranged contact surfaces for contacting the femoral neck or head to better accommodate a variety of different component configurations and/or impingement conditions provided by orthopaedic hip arthroplasty implant systems to reduce contact stress between the insert and the femoral neck or head.

In accordance with one or more features of the present disclosure, as will be described in greater detail below, an insert arranged and configured for use in a dual mobility acetabular bearing for incorporation into a dual mobility acetabular implant is disclosed. The insert includes a plurality or multiple chamfers positioned at the rim of the insert. Thus arranged, the insert provides multiple different and distinct contact surfaces for contacting the femoral neck of an associated hip implant system at the point of impingement with the insert. By providing increased contact surfaces, line contact between the rim of the insert and the femoral neck can be achieved for a wide variety of component combinations thereby reducing contact stress therebetween and thus reducing the degree of deformation damage from intermittent impingement, which increases the long-term attachment strength between the femoral neck or head and the insert (e.g., by providing variable rim geometries, the insert is better able to accommodate any number of different femoral neck and head configurations as opposed to current inserts, which only utilize a single chamfer optimized for a limited number of femoral neck and head combinations).

Generally speaking, a dual mobility acetabular implant is arranged and configured to be positioned within a patient's acetabulum and may be used in combination with a femoral or hip implant such as, for example, femoral or hip implant 175 illustrated in FIG. 1. In one embodiment, the acetabular implant such as, for example, acetabular implant 100, may include an acetabular cup such as, for example, acetabular cup 110, a liner such as, for example, liner 120, and a femoral head such as, for example, femoral head 170 of hip implant 175. In addition, the acetabular implant includes an insert positioned between the liner and the femoral head.

As will be appreciated by one of ordinary skill in the art, the acetabular cup is arranged and configured to be implanted into the patient's acetabular region (e.g., patient's acetabulum). The acetabular cup may be secured to the patient's acetabulum via, for example, fasteners, adhesive, cement, or combinations thereof, etc. For example, the acetabular cup may include a hollow body (hereinafter "body") extending from an annular rim to an apex or polar end thereof. The body includes a hollow interior cavity, a generally curved or convex outer exterior surface, and a generally curved or concave interior surface. In addition, the acetabular cup may include one or more fastener openings arranged and configured to receive one or more bone fasteners (not shown).

The liner is arranged and configured to be inserted into the interior cavity of the acetabular cup. The liner may be coupled to the acetabular cup via, for example, an adhesive, cement, etc. Thus, once the cement hardens, the liner may be inhibited from moving, articulating, or the like, relative to the acetabular cup. For example, the liner may include a hollow body extending from an annular rim to an apex or polar end thereof. The body including a hollow interior cavity, a generally curved or convex outer exterior surface, and a generally curved or concave interior surface.

In accordance with one or more features of the present disclosure, the dual mobility acetabular implant incorporates an improved insert as will be described herein. For example, referring to FIGS. 2A-2C, a non-limiting example embodiment of an insert 240 in accordance with one or more features of the present disclosure is illustrated. In use, the insert 240 is arranged and configured to be used in a dual mobility acetabular implant such as, for example, dual mobility acetabular implant 100. In use, the insert 240 is used in place of conventional inserts 140 in an acetabular implant 100. As illustrated, the insert 240, as will be described in greater detail below, includes a plurality of chamfers of varied geometries based on a variety of impingement conditions presented by families of stemmed femoral implants and femoral head designs offered by manufacturers. Thus arranged, the insert 240 is arranged and configured to provide an increased contact surface for most configurations while providing a reduced angle of incidence between the femoral neck and annular rim of the insert 240.

Figure 2A:
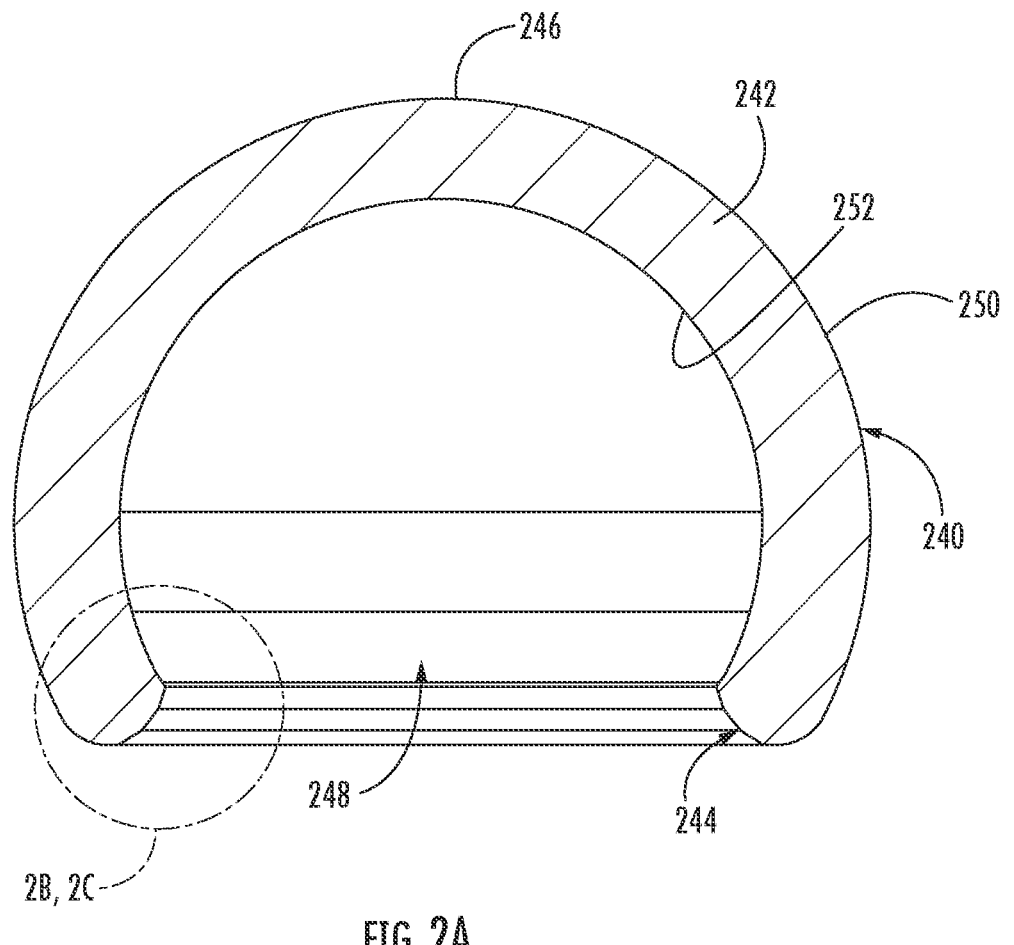
FIG. 2A shows a cross-sectional view of an example of an embodiment of an insert in accordance with one or more features of the present disclosure, the insert being arranged and configured to be incorporated into a dual mobility acetabular implant such as, for example, the dual mobility acetabular implant of FIG. 1.

Referring to FIG. 2A, the insert 240 is arranged and configured to be received within the interior cavity of the liner. In addition, the insert 240 is arranged and configured to receive a femoral head such as, for example, femoral head 170 of the hip or femoral implant 175. In use, the insert 240 is arranged and configured to articulate within and relative to the liner and the femoral head is arranged and configured to articulate within and relative to the insert 240. As illustrated, in one embodiment, the insert 240 includes a hollow body 242 (hereinafter "body") extending from an annular rim 244 to an apex or polar end 246 thereof. The body 242 including a hollow interior cavity 248. The body 242 may define a generally curved or convex outer exterior surface 250 arranged and configured to articulate relative to an inner surface of the interior cavity of the liner and a generally curved or concave interior surface 252 arranged and configured to articulate relative to an outer surface of the femoral head. Thus arranged, the insert 240 includes a convex, generally spherical outer bearing surface which articulates against the liner and a concave, generally spherical, inner bearing surface which articulates against the convex, femoral head, which may be coupled to a femoral neck via, for example, a mechanical taper lock.

In use, the insert 240 may be coupled to or receive the femoral head by any mechanism now known or hereafter developed. In one embodiment, the insert 240 may be arranged and configured to snap-fit over the femoral head in order to retain the femoral head and prevent unintended escape or dislocation of the femoral head from the insert 240.

Figure 6A:
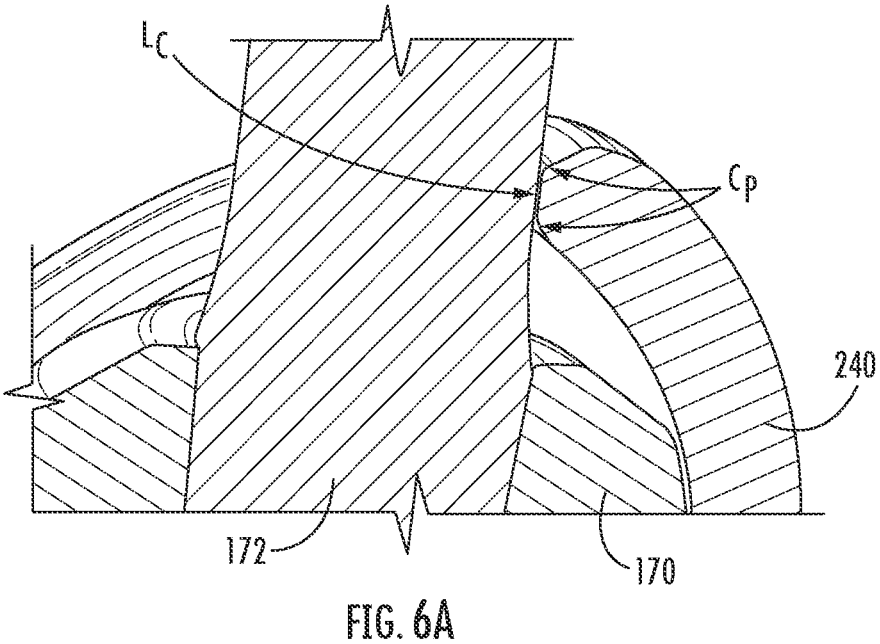
FIGS. 6A and 6B illustrate alternate, detailed views of an example of an embodiment of an annular rim of an insert contacting a femoral neck of a hip implant in accordance with one or more features of the present disclosure.
Figure 6B:
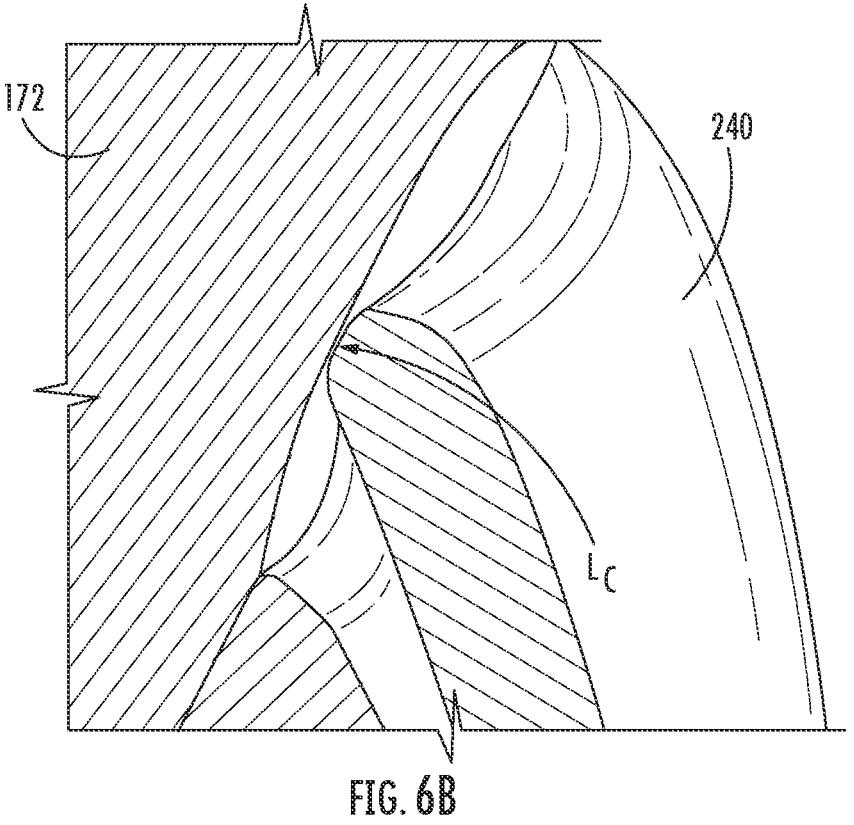

In accordance with one or more features of the present disclosure and in contrast to conventional dual mobility inserts that include a single annular chamfer at the rim thereof, the insert 240 according to features of the present disclosure include a plurality of chamfers defining multiple contact surfaces or areas for contacting the femoral component (e.g., neck or head). For example, referring to FIGS. 2A-2C, in one embodiment, the insert 240 may include a rim 244 including first, second, and third chamfers defining first, second, and third contact surfaces 260, 262, 264, although this is one configuration and the rim may include a different number of chamfers defining a different number of contact surfaces such as, for example, two chamfers, four chamfers, etc. In use, each of the chamfers define a contact area or surface arranged and configured to contact, for example, the femoral neck of the hip implant. In use, each of the contact areas or surfaces 260, 262, 264 is arranged and configured to contact the femoral neck depending on a different configuration of femoral neck and femoral head combination (e.g., depending on the surgeon selected combination of femoral neck and femoral head, the insert includes a contact area or surface arranged and configured to contact the femoral neck to reduce the contact stress during use). Thus, in use, the insert 240 may include two or three different contact areas or surfaces 260, 262, 264 designed for different femoral combinations. As a result, the insert 240 is better able to accommodate different surgeon selected combinations of neck and/or heads. Thus, in accordance with features of the present disclosure, the insert 240 is better able to ensure that contact between the contact surfaces or areas 260, 262, 264 on the rim 244 of the insert 250 and the femoral neck initiates with a decreased line contact stress condition with an approximate cylinder-to-cylinder condition thus increasing the length or area over which contact stress is distributed (e.g., as illustrated in FIGS. 6A and 6B, and as will be described in greater detail below by way of example, incorporation of a plurality of chamfers defining multiple contact areas or surfaces ensures that the insert 240 in accordance with the features of the present disclosure contacts the femoral neck 172 along a line LC extending between adjacent chamfer points CP. Thus arranged, a cylindrical line contact stress condition is achieved). Thus, by incorporating multiple chamfers and/or contact surfaces, reduced stress impingement conditions are created for a variety of different femoral combinations across different product lines and variants within each product line.

Figure 2B:
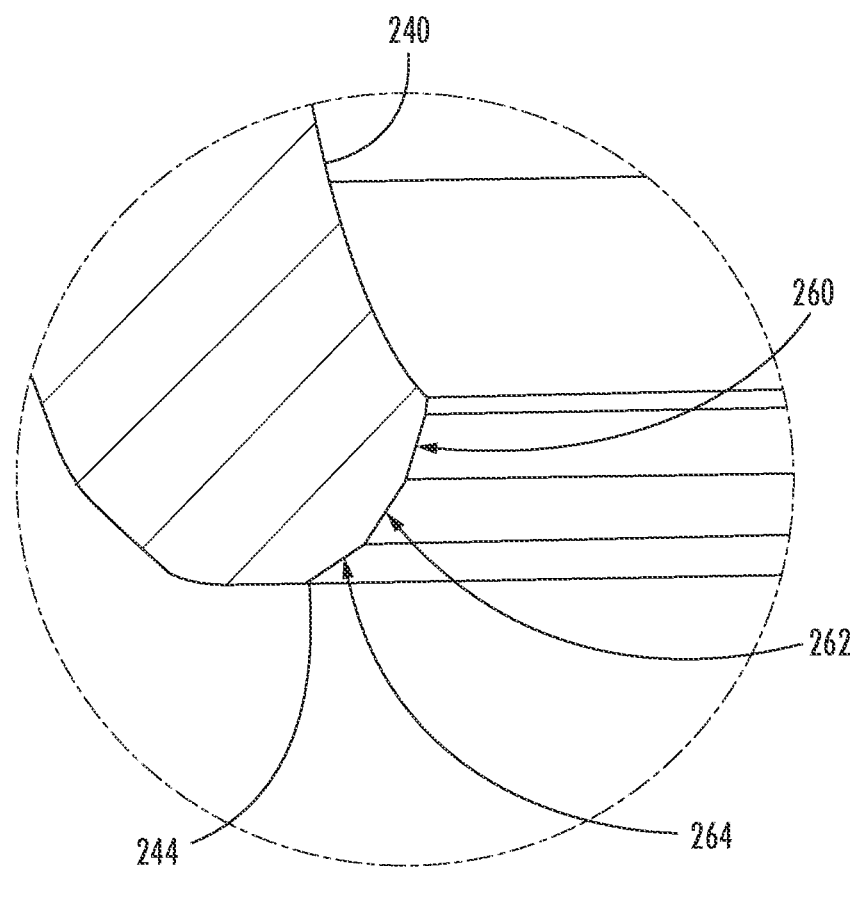
FIG. 2B shows a detailed view of an example of an embodiment of an annular rim of the insert shown in FIG. 2A.
Figure 2C:
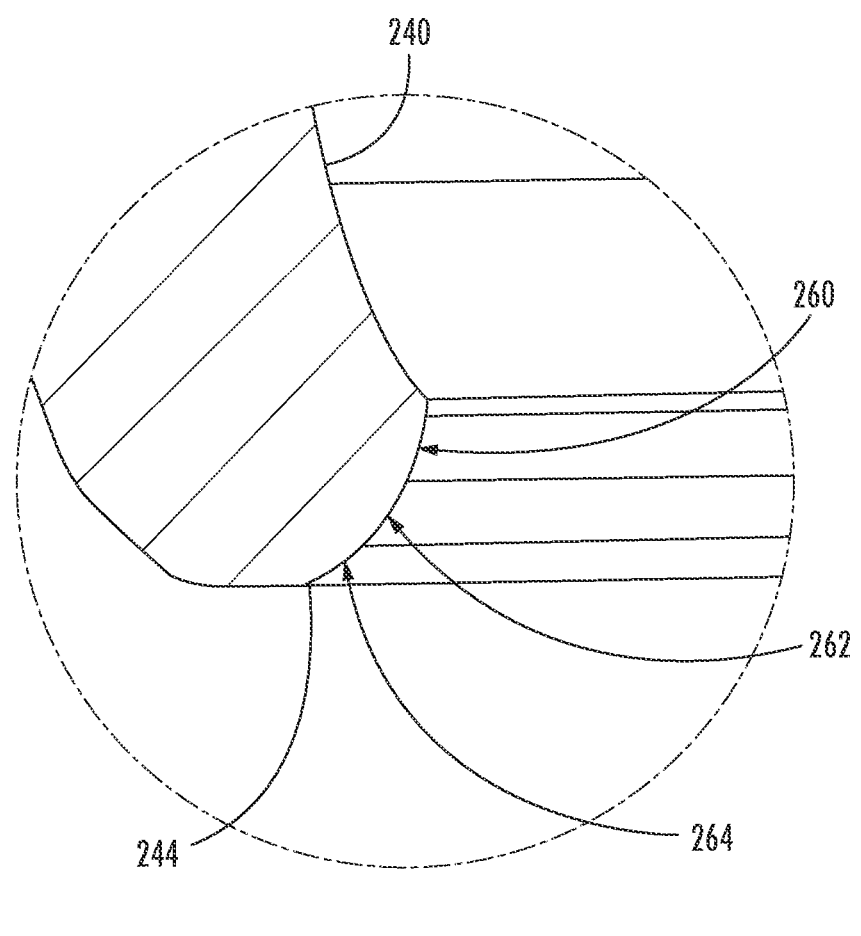
FIG. 2C shows a detailed view of an alternate example of an embodiment of an annular rim of the insert shown in FIG. 2A.

For example, referring to FIG. 2B, in one example embodiment, the insert 240 includes a rim 244 including plurality of chamfer angles defining a plurality of contact surfaces or areas 260, 262, 264 designed to accommodate or correspond with a different femoral head length at the rim thereof. As illustrated, in one embodiment, the plurality of contact surfaces or areas 260, 262, 264 may include sharp transitions therebetween. Alternatively, referring to FIG. 2C, radiused transitions can be utilized between the plurality of contact surfaces or areas 260, 262, 264 rather than conical chamfers to present a relatively broader contact surface as compared to the sharp transitions.

Figure 3A:
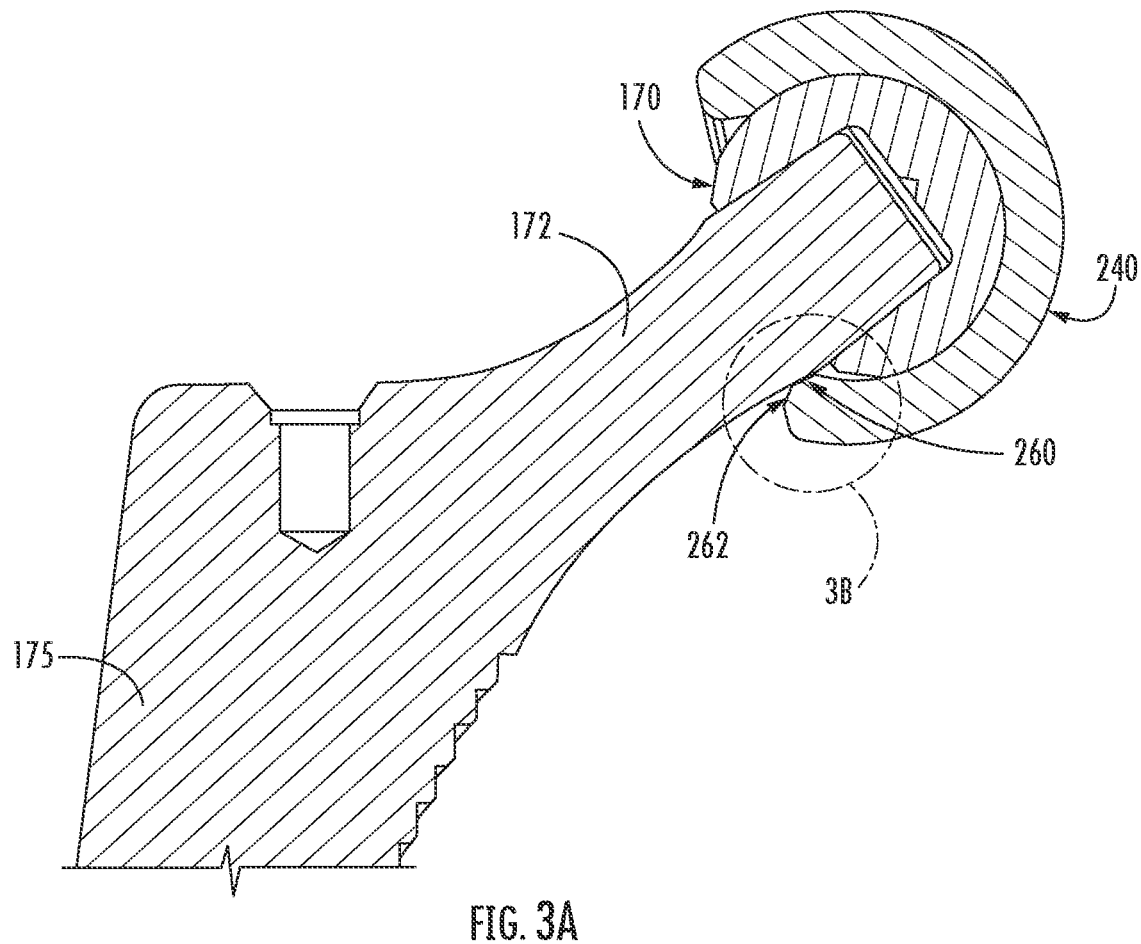
FIG. 3A shows a cross-sectional view of an example of an embodiment of an insert in accordance with one or more features of the present disclosure, the insert coupled to a hip implant including a femoral neck and a femoral head.
Figure 3B:
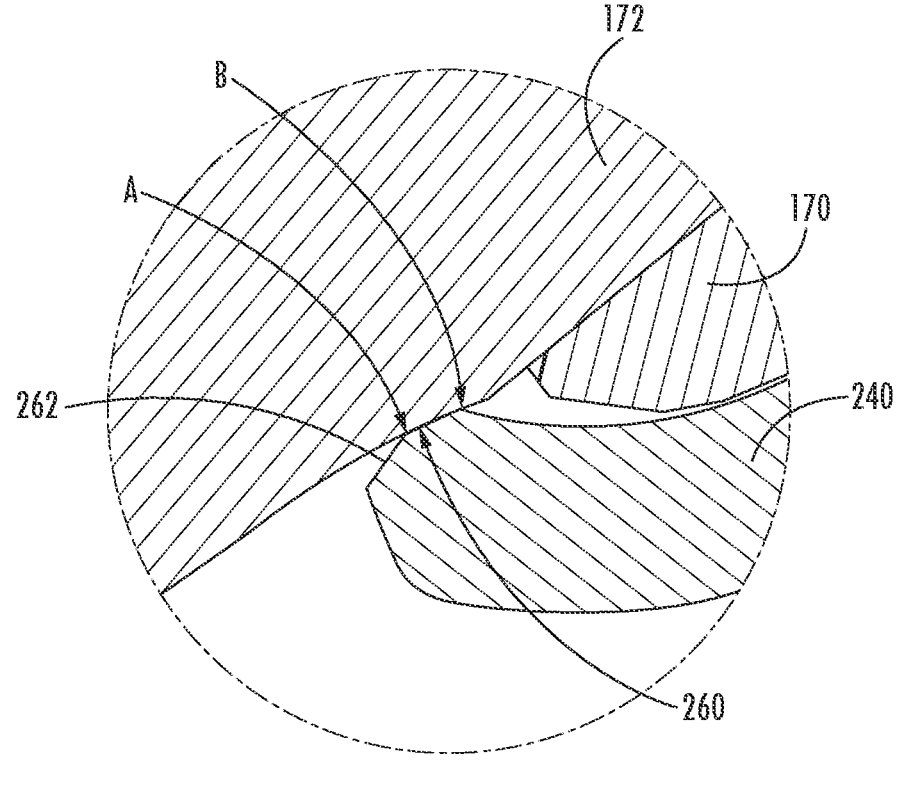
FIG. 3B shows a detailed view of an example of an embodiment of an annular rim of the insert shown in FIG. 3A contacting the femoral neck of the hip implant.

Referring to FIGS. 3A and 3B, in one combination of femoral neck 172 and femoral head 170, the insert 240, which is illustrated in full rotation so as to be in contact with the femoral neck 172, includes first and second chamfers defining first and second contact surfaces or areas 260, 262 arranged and configured to provide increased contact with the femoral neck 172. For example, as best illustrated in FIG. 3B, the first and second chamfers define a contact surface 260 extending from point A to point B. As illustrated, in FIGS. 3A and 3B, the selected femoral head 170 has a given head length arranged and configured to generate a first impingement condition between the insert 240 and femoral neck 172 just distal to the locking taper of the implant 175. In use, when the insert 240 is rotated sufficiently so that the rim 244 of the insert 240 contacts the femoral neck 172, the first contact surface 260 extending between point A to point B contacts the femoral neck 172.

Figure 4A:
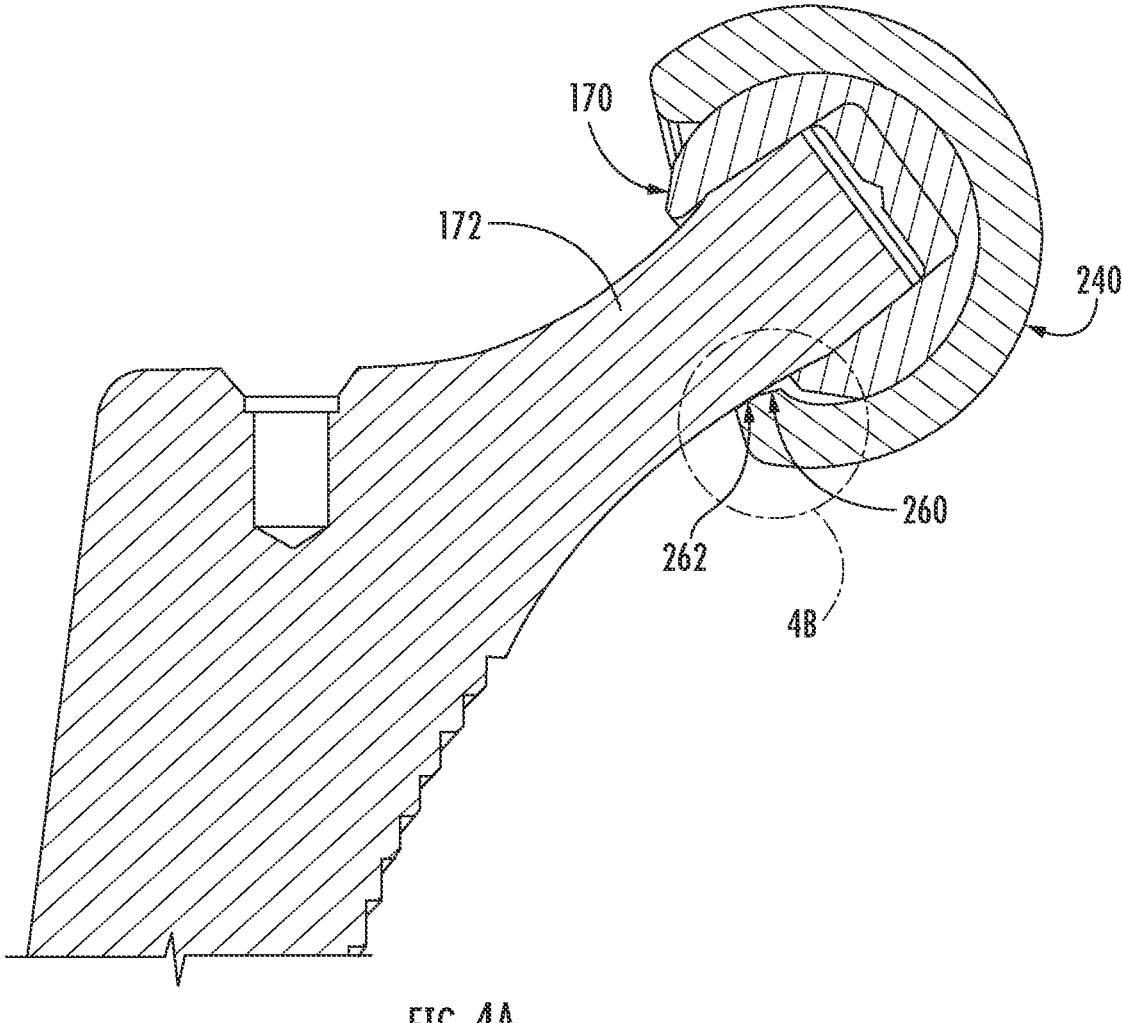
FIG. 4A shows a cross-sectional view of an example of an embodiment of an insert in accordance with one or more features of the present disclosure, the insert coupled to a hip implant including an alternate femoral neck and femoral head combination.
Figure 4B:
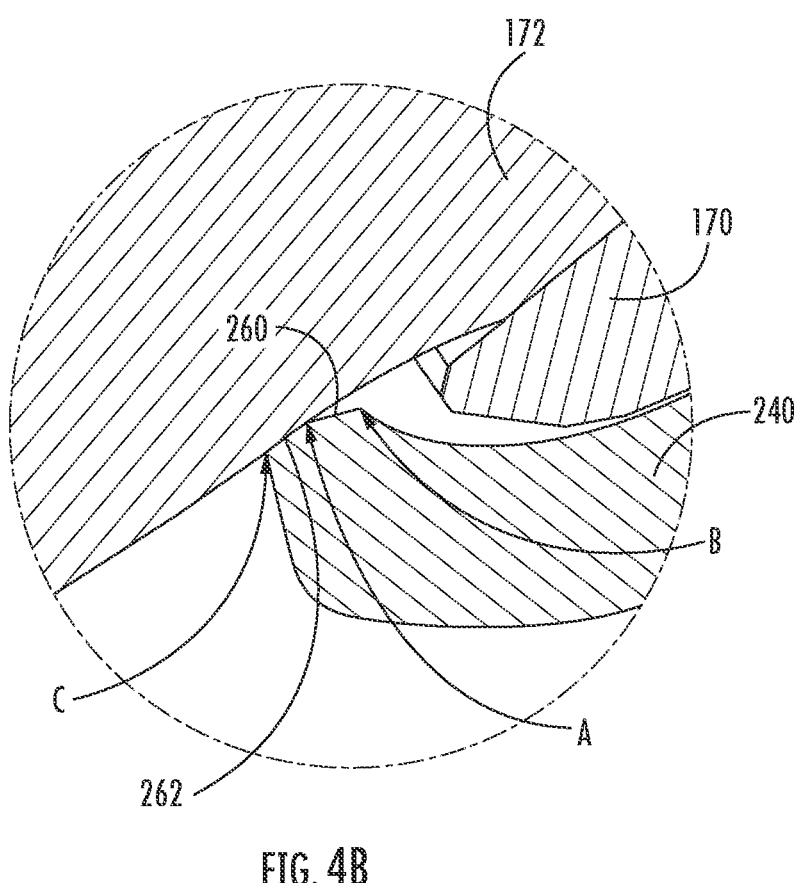
FIG. 4B shows a detailed view of an example of an embodiment of an annular rim of the insert shown in FIG. 4A contacting the femoral neck of the hip implant.

However, referring to FIGS. 4A and 4B, when a different femoral neck 172 is chosen (e.g., a femoral implant having a neck of different length, diameter, geometry, etc.), a second impingement condition is created. In this combination, when the insert 240 is rotated sufficiently so that the rim 244 of the insert 240 contacts the femoral neck 172, the second contact surface 262 extending between point A and point C contacts the femoral neck 172. The contact area or surface 262 is arranged and configured to provide increased contact with the femoral neck 172. For example, the chamfer defines a contact surface 262 extending from point A to point C (e.g., the edge highlighted by point A being transition from chamfer AB to chamfer AC). Thus, by incorporating a plurality of chamfers defining a plurality of contacts surfaces for contacting the femoral neck, the insert 240 is arranged and configured to accommodate different femoral components thereby reducing contact stress and preventing, or at least minimizing, the possibility for dislocation.

Figure 5A:
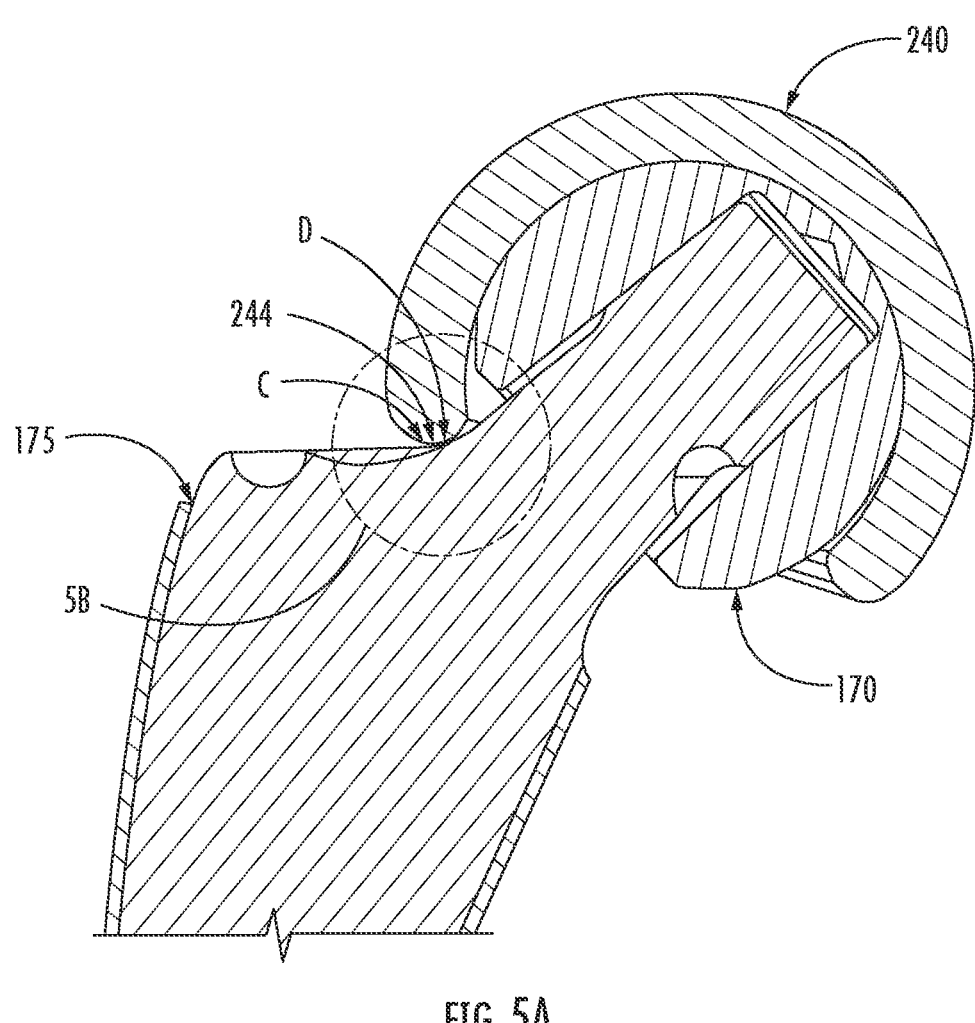
FIG. 5A shows a cross-sectional view of an example of an embodiment of an insert in accordance with one or more features of the present disclosure, the insert coupled to a hip implant including an alternate femoral neck and femoral head combination.
Figure 5B:
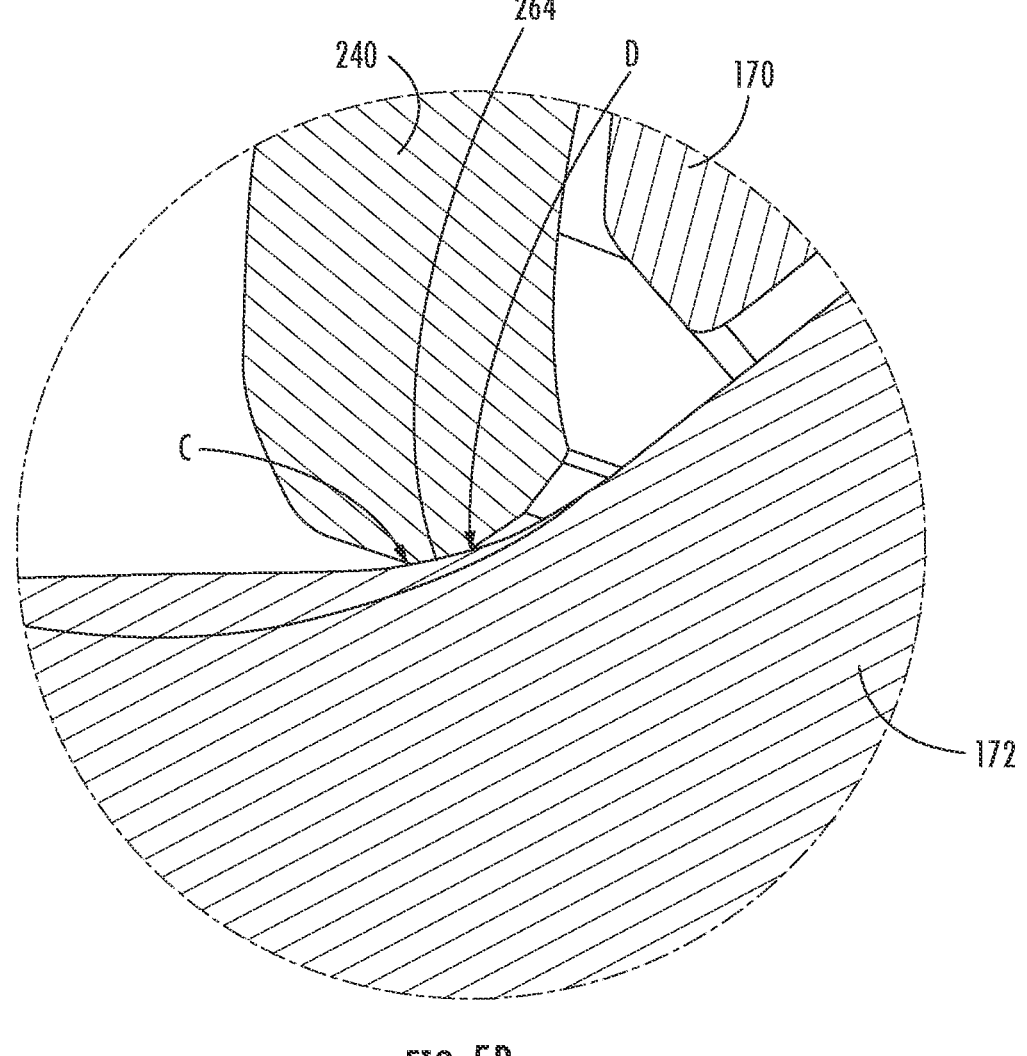
FIG. 5B shows a detailed view of an example of an embodiment of an annular rim of the insert shown in FIG. 5A contacting the femoral neck of the hip implant.

Similarly, referring to FIGS. 5A and 5B, when a different femoral neck is chosen, (e.g., a femoral implant having a neck of different length, diameter, geometry, etc.), a third impingement condition is created. For example, in the illustrated embodiment, the femoral implant includes a larger diameter femoral head, which, in use, changes the angle of impingement between the insert and the femoral neck (e.g., a larger femoral head allows greater angulation before impingement and change to the angle of the chamfer). In this combination, when the insert 240 is rotated sufficiently so that the rim 244 of the insert 240 contacts the femoral neck 172, a third chamfer defining a third contact area or surface 264 is provided to provide increased contact with the femoral neck. For example, the chamfer defines a contact surface 264 extending from point C to point D (e.g., the edge highlighted by point C being transition from chamfer AC to chamfer CD). Once again, by incorporating a plurality of chamfers defining a plurality of contacts surfaces for contacting the femoral neck, the insert 240 is arranged and configured to accommodate different femoral components thereby reducing contact stress and preventing, or at least minimizing, the possibility for dislocation.

In accordance with additional features of the present disclosure, in one example of an embodiment, the insert 240 may be arranged and configured with an eccentric head center (e.g., eccentric or inner and outer articulating surfaces arranged with an offset). For example, in one embodiment, a rotational center point of the inner bearing surface may be offset (e.g., lateralized, medialized, or eccentric) relative to a rotational center point of the outer bearing surface. Alternatively, and/or in addition, a rotational center point of the insert 240 (e.g., the inner and/or outer bearing surface) may be offset (e.g., lateralized, medialized, or eccentric) relative to a rotational center point of the acetabular cup and/or liner. It has been discovered that by incorporating an eccentric head center, the insert 240 is better able to track the motion of the femoral head. For example, internal/external rotation of the insert 240 at the outer articulation surface tracks internal/external articulation of the inner articulation surface (e.g., articulation of the eccentric insert tends to track more closely with the load vector and motion of the femoral head). Additional information on eccentric inserts can be found in United States Published Patent Application No. 2019/0254827 (application Ser. No. 16/342,120, published on Aug. 22, 2019, entitled Lateralized Dual-Mobility Assembly, the entire contents of which are incorporated by reference herein.

In use, in one example method of use, the patient's acetabulum may be exposed and assessed identifying the location of quality bone. As needed, the acetabulum may be reconstructed using various instruments such as, impactors, reamers, etc. Next, the acetabular cup may be positioned and secured into the target host bone. For example, the surgeon may elect to position the acetabular cup into the patient's host bone to achieve optimal placement of the acetabular cup relative to the bone. The acetabular cup may be impacted into the target host bone and, in some embodiments, one or more optional fasteners may be inserted thru the cup and into the host bone. Next, the liner may be positioned within an interior cavity of the acetabular cup. The liner may be secured to the cup via, for example, cement, adhesive, or the like. The cement may be inserted, injected, or the like into the interior cavity of the cup to, inter alia, facilitate better coupling between the liner and the cup. The cement may be inserted, injected, or the like prior to insertion of the liner into the cup. Alternatively, the cement may be inserted, injected, or the like into the cup after the liner has been positioned within the cup. For example, in one embodiment, the liner may include annular and/or longitudinal grooves or ridges to facilitate cement injection and/or fixation. Finally, the dual mobility bearing including, for example, the insert 240 and the femoral head component may be positioned within the interior cavity of the liner.

Although non-limiting, the acetabular cup may be made from many different materials including zirconium, zirconium alloys (e.g., Zr-2.5Nb, among others), titanium, titanium alloys (e.g., Ti-6Al-4V or Ti-6AL-4V ELI, among others), tantalum, hafnium, niobium and any combination thereof, or cobalt-chromium alloys and stainless steel, among others. In some embodiments, the exterior surface may be porous. In addition, the cup may be a combination of different biocompatible materials. For example, the cup may be cobalt chrome with a porous titanium coating on the exterior surface. Various manufacturing techniques may be used to manufacture the cup. For example, additive manufacturing techniques include those known in the art such as solid free-form fabrication (SFF), selective laser sintering (SLS), direct metal fabrication (DMF), direct metal laser sintering (DMLS), electron beam melting (EBM), and selective laser melting (SLM), among others. Additive manufacturing methods allow for three-dimensional structures to be constructed one layer at a time from a powder which is solidified by irradiating a layer of powder with an energy source such as a laser or an electron beam. The powder may be selectively melted in some regions, thereby forming substantially nonporous regions. In other regions, the lack of fused powder provides porous regions. Such substantially nonporous regions and porous regions can be formed by the application of energy from the energy source, which may be directed in raster-scan fashion to selected portions of the powder layer to melt, fuse and/or sinter the powder. After forming a pattern in one powder layer, an additional layer of powder is dispensed, and the process is repeated until the desired structure is complete.

Similarly, although non-limiting, the liner and/or the dual articulating bearing including, for example, the insert 240 and the femoral head component, may be formed of any suitable material now known or hereafter developed. For example, the insert 240 and the femoral head component may be manufactured from a polymeric material including, for example, a polyethylene material such as ultra-high molecular weight polyethylene, a highly cross-linked polyethylene, an anti-oxidant or antiseptic infused highly cross-linked polyethylene, PEEK, etc. The liner 120 may be manufactured from ceramic or metallic materials selected from groups consisting of zirconium, zirconium alloy, titanium, tantalum, hafnium, niobium and any combination thereof, or cobalt-chromium alloys and stainless steel, among others. In use, the bearing surfaces provide an articulating surface for the femoral head component to articulate relative to the insert 240 and for the insert 240 to articulate relative to the liner to track and accommodate the relative movement between the femur and the acetabulum. In one embodiment, the insert 240 may be manufactured from a highly cross-linked ultra-high molecular weight polyethylene (UHMWPE) to reduce wear and/or the insert 240 may incorporate a hydrophilic, low-friction bearing surface such as, for example, oxinium, ceramic, or the like. Alternatively, and/or in addition, the insert 240 may be diffusion hardened such as carburization or incorporate diamond, and diamond-like coatings as a low-friction surface. It has been discovered that by incorporating an eccentric rotational design and/or manufacturing the insert 240 from UHMWPE and/or utilizing a hydrophilic, low-friction bearing surface, the insert's ability to mitigate degradation and thus better able to prevent, or at least inhibit, unintended dislocation or removal of the femoral head from the insert is provided.

In some embodiments, the liner and acetabular cup may include surface features adapted and configured to allow for improved cement adhesion between the liner and cup. The surface features may be provided in any suitable manner now known or hereafter developed including, for example, grooves, recesses, indentations, etc., formed along an exterior surface of the liner. The surface features may be oriented radially, spherically, or both. In various embodiments, the surface features may be arranged and configured to ensure a minimum distance between the liner and the cup for receiving cement.

While the present disclosure refers to certain embodiments, numerous modifications, alterations, and changes to the described embodiments are possible without departing from the sphere and scope of the present disclosure, as defined in the appended claim(s). Accordingly, it is intended that the present disclosure not be limited to the described embodiments, but that it has the full scope defined by the language of the following claims, and equivalents thereof. The discussion of any embodiment is meant only to be explanatory and is not intended to suggest that the scope of the disclosure, including the claims, is limited to these embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art.

The foregoing discussion has been presented for purposes of illustration and description and is not intended to limit the disclosure to the form or forms disclosed herein. For example, various features of the disclosure are grouped together in one or more embodiments or configurations for the purpose of streamlining the disclosure. However, it should be understood that various features of the certain embodiments or configurations of the disclosure may be combined in alternate embodiments, or configurations.

As used herein, an element or step recited in the singular and proceeded with the word "a" or "an" should be understood as not excluding plural elements or steps, unless such exclusion is explicitly recited. Furthermore, references to "one embodiment" of the present disclosure are not intended to be interpreted as excluding the existence of additional embodiments that also incorporate the recited features.

The phrases "at least one", "one or more", and "and/or", as used herein, are open-ended expressions that are both conjunctive and disjunctive in operation. The terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., engaged, attached, coupled, connected, and joined) are to be construed broadly and may include intermediate members between a collection of elements and relative to movement between elements unless otherwise indicated. As such, connection references do not necessarily infer that two elements are directly connected and in fixed relation to each other. All rotational references describe relative movement between the various elements. Identification references (e.g., primary, secondary, first, second, third, fourth, etc.) are not intended to connote importance or priority but are used to distinguish one feature from another. The drawings are for purposes of illustration only and the dimensions, positions, order and relative to sizes reflected in the drawings attached hereto may vary.

The invention claimed is:

1. A dual mobility acetabular implant comprising:
   an acetabular cup arranged and configured to be positioned within a patient's acetabulum, the acetabular cup including a body having an interior cavity;
   a liner arranged and configured to be inserted into the interior cavity of the acetabular cup, the liner including a body having an interior cavity; and
   an insert arranged and configured to be inserted into the interior cavity of the liner, the insert including a body extending from an annular rim to a polar end, the body including an interior cavity, a convex exterior surface arranged and configured to articulate relative to an inner surface of the interior cavity of the liner, and a concave interior surface arranged and configured to receive and articulate relative to an outer surface of a femoral head;
   wherein the annular rim of the insert includes a plurality of chamfers defining multiple contact surfaces for contacting a portion of a femoral neck, wherein the plurality of chamfers comprise first, second, and third chamfers defining first, second, and third distinct contact surfaces, each of the first, second, and third distinct contact surfaces arranged and configured to contact the femoral neck.

2. The dual mobility acetabular implant of claim 1, wherein the first, second, and third distinct contact surfaces are arranged and configured to accommodate a variety of different femoral component configurations or impingement conditions in order to reduce contact stress between the insert and the femoral neck.

3. The dual mobility acetabular implant of claim 1, wherein the annular rim includes a first angled transition between the first and second contact surfaces and a second angled transition between the second and third contact surfaces.

4. The dual mobility acetabular implant of claim 1, wherein the annular rim includes a first radiused transition between the first and second contact surfaces and a second radiused transition between the second and third contact surfaces.

5. The dual mobility acetabular implant of claim 1, wherein the first contact surface is arranged and configured to contact the femoral neck during a first impingement condition and the second contact surface is arranged and configured to contact the femoral neck during a second impingement condition.

6. The dual mobility acetabular implant of claim 5, wherein the third contact surface is arranged and configured to contact the femoral neck during a third impingement condition.

7. The dual mobility acetabular implant of claim 1, wherein the insert is manufactured from a highly cross-linked ultra-high molecular weight polyethylene (UHMWPE).

8. The dual mobility acetabular implant of claim 1, wherein the insert includes a hydrophilic, low-friction bearing surface.

* * * * *